July 27, 1948. H. F. SMITH Plant Pat. 803

PEACH TREE

Filed May 14, 1947

Inventor
H. F. Smith
By Robb & Robb
Attorneys

Patented July 27, 1948

Plant Pat. 803

UNITED STATES PATENT OFFICE

803

PEACH TREE

Henry Frank Smith, Dover, Ark., assignor to Stark Bro's Nurseries and Orchards Company, Louisiana, Mo., a corporation of Missouri Application May 14, 1947, Serial No. 747,934

1 Claim. (Cl. 47—62)

The present discovery relates to a new and distinct variety of peach tree, originating as a sport of the well known variety "Burbank's July Elberta." This known variety has proved to be one of the most popular and valued of yellow-fleshed, freestone peaches, because of the excellence of its uniform-sized fruit, which colors early and completely.

The new bud sport variety herein described is substantially identical with its parent, when grown under comparable conditions, as to all dominant characteristics, excepting only as to its ripening season. This new peach ripens approximately eighteen days before "Burbank's July Elberta" (Pl. Pat. No. 15).

Asexual reproduction shows that these characteristics hold true through succeeding propagations.

Figure 1:
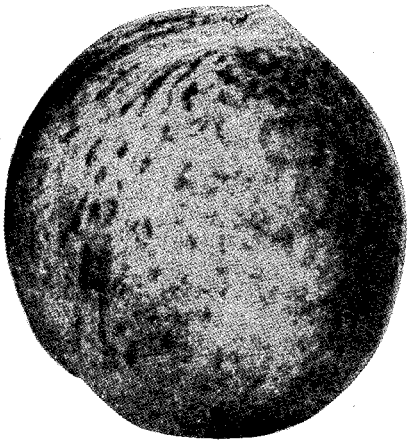
Figure 2:
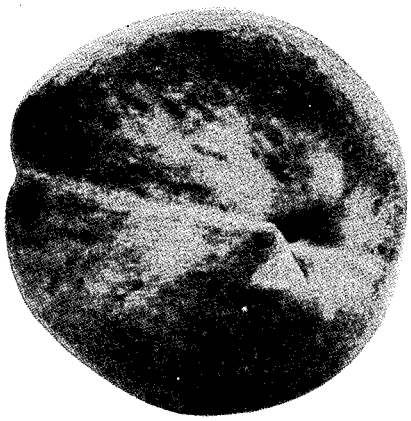

The accompanying drawing shows specimens of the fruit of the new variety, depicting clearly the shape, size and form from different angles. In the drawings, Figures 1 and 2 are obverse elevation views of specimens of this new variety.

The following is a detailed description of the new variety, giving color designations according to the conventional dictionary definition of terminology as well as corresponding color terms according to Ridgway's Color Standard:

Dates of first and last picking: July 13th–July 20th, at Atlas, in the county of Pike, and State of Illinois.

Tree: Medium large; medium vigorous; open; spreading; vase formed; hardy; very productive; regular bearer.

Trunk: Medium stocky; medium smooth.

Branches: Medium slender; smooth; glossy. Color—Hessian Brown, Plate XIII, Color 5′, Tone *m*.

*Lenticles.*—numerous; medium large.

Leaves: Length—5½ inches; width—1¼ inches. Medium large; oval; acutely pointed; medium thick; rugose.

*Color.*—Forest Green, Plate XVII, Color 29′, Tone *m*.

*Margin.*—Finely serrate.

*Petiole.*—medium short and slender.

*Glands.*—average number—2–6. Opposite; medium small; reniform; free.

Flowers: Dates first and full blossoms—March 27th–March 29th, the same as Burbank's July Elberta. Small; pink.

Fruit: Eating—July 15th.

*Size.*—Uniform; medium large. Axial diameter—2⅞ inches. Transverse in suture plane—2¾ inches. At right angles to suture plane—2¾ inches.

*Form.*—Symmetrical; globose. Suture—distinct; deep; extends from base to beyond apex; marked depression beyond pistil point. Ventral surface—strongly lipped toward apex throughout left side. Lips—unequal.

*Cavity.*—Abrupt; elongated in suture plane showing on both sides. Depth—½ inch. Breadth—⅝ inch.

*Base.*—Cuneate; oblique.

*Apex.*—Short; rounded; apical.

*Stem.*—Stout; glabrous; strong.

*Skin.*—Medium thin; medium tough; free. Tendency to break—none. Color—Carmine, Plate I, Color 1, Tone *i*. Down—Scant; short. Does not roll up when rubbed.

Flesh: *Color.*—Deep Chrome, Plate III, Color 17, Tone *b*. Mottled with Scarlet Red, Plate 1, Color 3, toward base. Surface of pit cavity—Pink.

*Texture.*—Firm.

*Fibres.*—Few; fine.

*Ripens.*—Fairly even.

*Flavor.*—Mild.

*Aroma.*—Distinct.

*Eating quality.*—Best.

Stone: Free when fully ripe.

*Fibres.*—Long; free on sides.

*Size.*—Medium small. Length—1⅝ inches. Thickness—⅞ inch.

*Form.*—Obovoid; cuneate toward base.

*Base.*—Oblique; narrow; oval.

*Apex.*—Acute.

*Sides.*—Equal; curved on right and left sides.

*Surface.*—Irregularly furrowed throughout; pitted throughout.

*Ridges.*—Rounded toward base.

*Pits.*—Circular to elongated. Ventral edge—Thin with wing toward base.

*Dorsal edge.*—Full with shallow, narrow groove toward base. Ridges—interrupted.

Use: Market; dessert; canning.

Keeping Quality: Medium good.

Resistance to: Insects—Good. Disease—Medium good.

Shipping Quality: Good.

I claim:

A new and distinct variety of peach tree, characterized as to novelty by its early ripening season, approximately eighteen days before its parent variety, substantially as described.

HENRY FRANK SMITH.